US011596807B2

(12) United States Patent
Maurer et al.

(10) Patent No.: US 11,596,807 B2
(45) Date of Patent: Mar. 7, 2023

(54) PARTIAL DEFORMATION MAPS FOR RECONSTRUCTING MOTION-AFFECTED TREATMENT DOSE

(71) Applicant: Accuray Incorporated, Sunnyvale, CA (US)

(72) Inventors: Calvin R. Maurer, San Jose, CA (US); Eric Schnarr, McFarland, WI (US); Rich Holloway, Chapel Hill, NC (US); Jacob Shea, Cross Plains, WI (US); Charles Brandon Frederick, Raleigh, NC (US); Kevin Gorczowski, Chapel Hill, NC (US); Robert Elijah Broadhurst, Carrboro, NC (US); Mark Foskey, Chapel Hill, NC (US)

(73) Assignee: Accuray Incorporated, Sunnyvale, CA (US)

(*) Notice: Subject to any disclaimer, the term of this patent is extended or adjusted under 35 U.S.C. 154(b) by 293 days.

(21) Appl. No.: 17/098,149

(22) Filed: Nov. 13, 2020

(65) Prior Publication Data
US 2021/0154494 A1 May 27, 2021

Related U.S. Application Data

(60) Provisional application No. 62/940,037, filed on Nov. 25, 2019.

(51) Int. Cl.
*A61N 5/10* (2006.01)
*G06N 3/08* (2006.01)
(Continued)

(52) U.S. Cl.
CPC .......... *A61N 5/1039* (2013.01); *A61N 5/103* (2013.01); *A61N 5/1031* (2013.01);
(Continued)

(58) Field of Classification Search
CPC .... A61N 5/103; A61N 5/1031; A61N 5/1037; A61N 5/1039; A61N 5/1049;
(Continued)

(56) References Cited

U.S. PATENT DOCUMENTS

2019/0183446 A1\* 6/2019 Mori ........................ A61B 6/54
2019/0333623 A1 10/2019 Hibbard

FOREIGN PATENT DOCUMENTS

| EP | 3501604 A1 | 6/2019 |
|----|------------|--------|
| WO | 2009054879 A1 | 4/2009 |
| WO | 2018048575 A1 | 3/2018 |

OTHER PUBLICATIONS

International Searching Authority, International Search Report and Written Opinion for application No. PCT/US2020/061115 dated Feb. 16, 2021.

\* cited by examiner

*Primary Examiner* — Mark R Gaworecki
(74) *Attorney, Agent, or Firm* — Womble Bond Dickinson (US) LLP (57) ABSTRACT

A method comprises identifying a treatment planning image of a target subject, the treatment planning image comprising information associated with an arrangement of structures within the target subject. The method further comprises generating, based on the information, a set of reference data associated with the target subject, the reference data indicating a plurality of positions of the target subject. The method further comprises generating target-subject-specific models based on the reference data and modifying one or more hyper-parameters of the target-subject-specific mode to generate second target-subject-specific models corresponding to a second position of the plurality of positions. The method further comprises controlling a radiation treatment delivery device based on the second target-subject- (Continued)

specific model to deliver a radiation treatment to the target subject.

46 Claims, 6 Drawing Sheets

(51) Int. Cl.
    *G06N 3/04*     (2006.01)
    *G06N 20/00*     (2019.01)
    *G06T 7/00*     (2017.01)
    *G06T 7/73*     (2017.01)
    *G06N 3/088*     (2023.01)
    *G06T 7/246*     (2017.01)
    *G06T 7/33*     (2017.01)
    *G06N 5/00*     (2023.01)

(52) U.S. Cl.
CPC ......... *A61N 5/1037* (2013.01); *A61N 5/1049* (2013.01); *A61N 5/1082* (2013.01); *G06N 3/0454* (2013.01); *G06N 3/08* (2013.01); *G06N 3/088* (2013.01); *G06N 20/00* (2019.01); *G06T 7/0012* (2013.01); *G06T 7/246* (2017.01); *G06T 7/344* (2017.01); *G06T 7/75* (2017.01); *A61N 5/1083* (2013.01); *A61N 2005/1051* (2013.01); *G06N 3/0472* (2013.01); *G06N 5/003* (2013.01); *G06T 2200/04* (2013.01); *G06T 2207/10076* (2013.01); *G06T 2207/10081* (2013.01); *G06T 2207/10116* (2013.01); *G06T 2207/10124* (2013.01); *G06T 2207/20081* (2013.01); *G06T 2207/20084* (2013.01); *G06T 2207/30096* (2013.01)

(58) Field of Classification Search
CPC ................ A61N 5/1082; A61N 5/1083; A61N 2005/1051; G06N 3/0454; G06N 3/0472; G06N 3/08; G06N 3/088; G06N 5/003; G06N 20/00; G06T 7/0012; G06T 7/246; G06T 7/344; G06T 7/75; G06T 2200/04; G06T 2207/10076; G06T 2207/10081; G06T 2207/10116; G06T 2207/10124; G06T 2207/20081; G06T 2207/20084; G06T 2207/30096
See application file for complete search history.

PARTIAL DEFORMATION MAPS FOR RECONSTRUCTING MOTION-AFFECTED TREATMENT DOSE

CROSS REFERENCE TO RELATED APPLICATIONS

This application claims the benefit of U.S. Provisional Application Ser. No. 62/940,037, filed Nov. 25, 2019, the disclosure of which is incorporated herein by reference in its entirety.

TECHNICAL FIELD

The present disclosure relates to partial deformation maps for reconstructing motion-affected treatment dose.

BACKGROUND

In radiation treatment, doses of radiation delivered via a radiation treatment beam from a source outside a patient's body are delivered to a target region in the body, in order to destroy tumorous cells. Care must be taken to minimize the amount of radiation that is delivered to non-treatment regions while maximizing the amount of radiation delivered by a treatment dose to the intended treatment regions.

BRIEF DESCRIPTION OF THE DRAWINGS

The present disclosure will be understood more fully from the detailed description given below and from the accompanying drawings of various implementations of the disclosure.

DETAILED DESCRIPTION

Embodiments of the present invention relate to the field of image guided treatment and, in particular, to a system for partial deformation maps for reconstructing motion-affected treatment. In various embodiments, the systems and methods provided herein describe generation and use of intra-patient transformation models from a single image for radiation therapy applications and reducing the effects of appearance changes on registration by generative image metamorphosis.

In one embodiment, a component of radiation treatment therapy may be estimating a transformation between the space of the planning image and that of the patient at treatment time. Ideally, this transformation could be obtainable at treatment time from some limited, low-latency sentinel information, such as 2-D projection images or optical marker positions, so that the transformation can be temporally accurate. Such transformations may be valuable to online adaptation in many forms, specifically with target tracking, dose accumulation, and predictive planning. In fact, if one has a good patient specific transformation model, the image analysis portion of adaptive radiotherapy may be solved.

In one embodiment, a credible transformation that can be determined from 2-D projections at treatment time may be describable by a small number of parameters (e.g., otherwise there may exist many possible transformations which would imply the same projections), and the space spanned by those parameters may consist of credible transformations (e.g., so that unlikely transformations are excluded from the search space). For example, if the transformation model describes respiration, all reasonable parameter choices should produce credible respirations. In sites affected by respiration, such models may be constructed using principal component analysis (PCA) amongst the phases of a respiration correlated computer tomography (RCCT). Similarly, registration of rigid and otherwise linear transformations, which have a small number of degrees of freedom by construction, may also be demonstrated.

In one embodiment, for respiratory motion models, the information used for model construction can be determined at planning time from an RCCT. This may not be the case for other sites, such as the pelvis, where transformations are observed over inter-fractional timescales. Furthermore, respiratory models may also be affected by these inter-fractional transformations, and the accuracy of such respiratory motion models and RCCTs in general may be subpar. Ideally, such a model would be constructible from a single planning image based on transformations observed in similar images and generalizable to likely transformations that the patient may undergo.

In one embodiment, a simple motion model can be constructed as follows: register all images together to form a somehow centrally located "mean" image and a set of transformations from the mean image to each of the phase images and perform PCA directly on the displacement vector fields produced by the group-wise registration. This results in a mean displacement vector $\mu$ and N eigenvectors v such that the linear combination of the first few eigenvectors well approximates all the transformations in the training set.

Considering the parameters as multipliers on the linear combination of the first 1-3 eigenvectors (the sum resulting in a displacement vector field) may produce a reasonable and credible patient specific respiration model with 1-3 parameters. These eigenvectors may be known as modes of variation. In one embodiment, a similar process may not be used for the male pelvis because the transformations are more complex than can be learned from a reasonable number of patient images. It is possible to construct a patient specific transformation model for the male pelvis, but the procedure above may not be successful in some situations. To resolve this problem and reduce the engineering complexity of this approach, there is a desire to combine transformation information from multiple patients into a single site-specific transformation model, which can then be applied to novel patients.

In one embodiment, to construct multi-patient transformation models, PCA models from several patients may be registered to a common atlas space, combined there, and then re-registered to a novel patient. In one embodiment, when modes of variation are transformed across the space of patient transformations to a common space, they undergo an unknown change.

While it is, or may be, possible to describe patient-specific transformation models with a linear dimensionality reduction, the failure of the previous approach suggests that the solution to the transport problem is non-linear.

This disclosure proposes a solution to this registration problem where, given a single patient planning image, a transformation model may be produced, which generates credible non-rigid transformations of that planning image that are likely to be observed over the course of treatment, such that the parameters of the transformation model (and thus the transformation) can be determined from a small number of 2-D projections.

As described herein, as a general concept, models may be fit to complex anatomic processes, which enables the inference of internal 3-D structures (and possibly appearances) of a subject from limited information. These models could be bio-mechanical in nature or generated via machine learning (e.g., by an auto-encoder neural network). For example, a full 3-D map of internal deformation of a patient could be inferred for every point in time of a treatment delivery, while only exposing the patient to infrequent 2-D image acquisitions. Another example would be to infer a full 3-D deformation map for a single moment in time from the limited data that could be acquired in the preceding fraction of a second.

Such systems and methods may be used in a variety of contexts. By way of non-limiting examples, the systems and methods described herein may be used for: real-time adaptation—adjusting a radiation therapy treatment in real-time to adapt to changes in the size & shape of the tumor and/or to changes in tumor position relative to other anatomical structures; dose reconstruction—calculating the dose delivered to a subject, while accounting for internal motion that affects the tumor, surrounding structures, and their positions relative to each other, and which occurred during the treatment delivery (e.g., lung tumor movement during treatment relative to the heart, spine, and abdomen, or bladder filling and rectal movement during treatment affecting the relative positions of the prostate, rectum, and bladder); 4-D imaging, including a) generating 3-D images of a subject for every point in time of a treatment or imaging procedure delivery, by calculating full 3-D deformation maps for each point in time and deforming a (pre-treatment) 3-D image though these maps, and b) generating better 4-D CT images by estimating the 3-D deformation map from just a few projections (possibly just one projection) and incorporating this into the back projection step of image reconstruction.

Further applications may include: real-time topographic imaging from 2-D x-ray views—by calculating a full 3-D deformation map from approximately the last second's worth of 2-D X-ray image data, and deforming a (pre-treatment) 3-D CT, it is possible to replicate the kind of display currently only available on MR-Linac systems—i.e., a real-time view of topographic image slices through the subject during treatment delivery. Because these topographic images are derived from a 3-D deformation map, it is also easy to propagate ROI contours from planning to overlay on the images. Similarly, you can propagate other image data that is co-registered with the planning image, such as functional data from MR and/or PET acquired offline with other systems. With such a function overlay, these real-time tomographic views could provide nearly all the same clinical benefit that would otherwise require an expensive MR-Linac treatment system.

In another example, the methods and systems described herein can be used as a predictor of biological response—this disclosure enables routine acquisition full 3-D deformation maps for every point in time from every treatment or imaging procedure. This in turn enables a broad class of analyses on changes in anatomy and motion patterns over time, which could be used to better model tumor response or other aspect of disease progression and treatment outcomes. For example: a) compute ventilation and changes in ventilation during treatment of lung patients; and b) compute stiffness and elastic properties of tissues and changes in stiffness and elastic properties in the lung, abdomen, and/or pelvis, possibly due to radiation damage In one embodiment, the terms "target," "target region," "target subject," etc. may refer to one or more fiducials near (within some defined proximity to) a treatment area (e.g., a tumor). In another embodiment, a target may be a bony structure.

In yet another embodiment a target may refer to soft tissue of a patient. A target may be any defined structure or area capable of being identified and tracked (including the entirety of the patient themselves) as described herein.

Figure 1A:
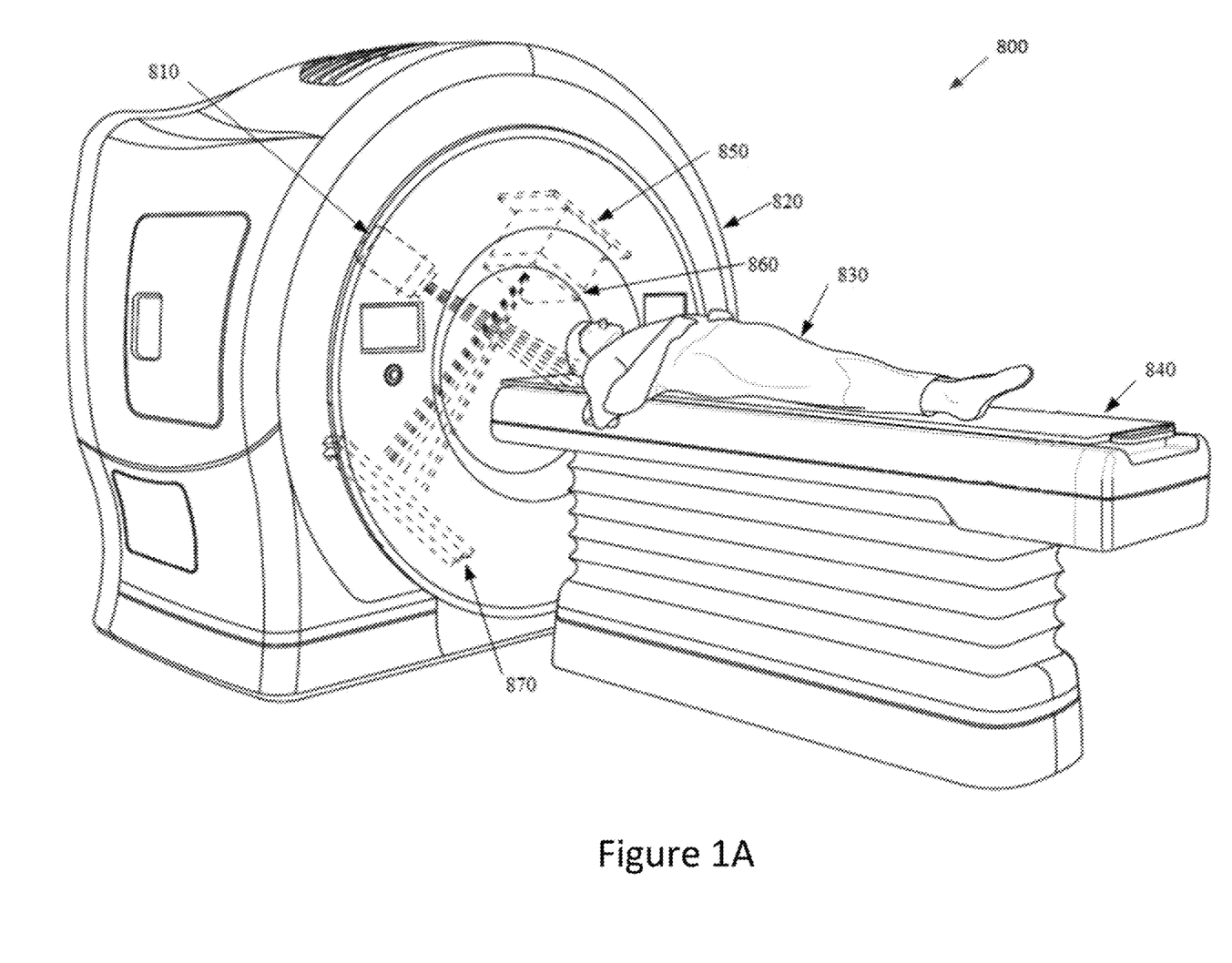
FIG. 1A illustrates a helical radiation delivery system, in accordance with embodiments described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC 860 may be an eMLC, as described herein. The MLC includes a housing that houses multiple leaves that are movable to adjust an aperture of the MLC to enable shaping of the treatment beam. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
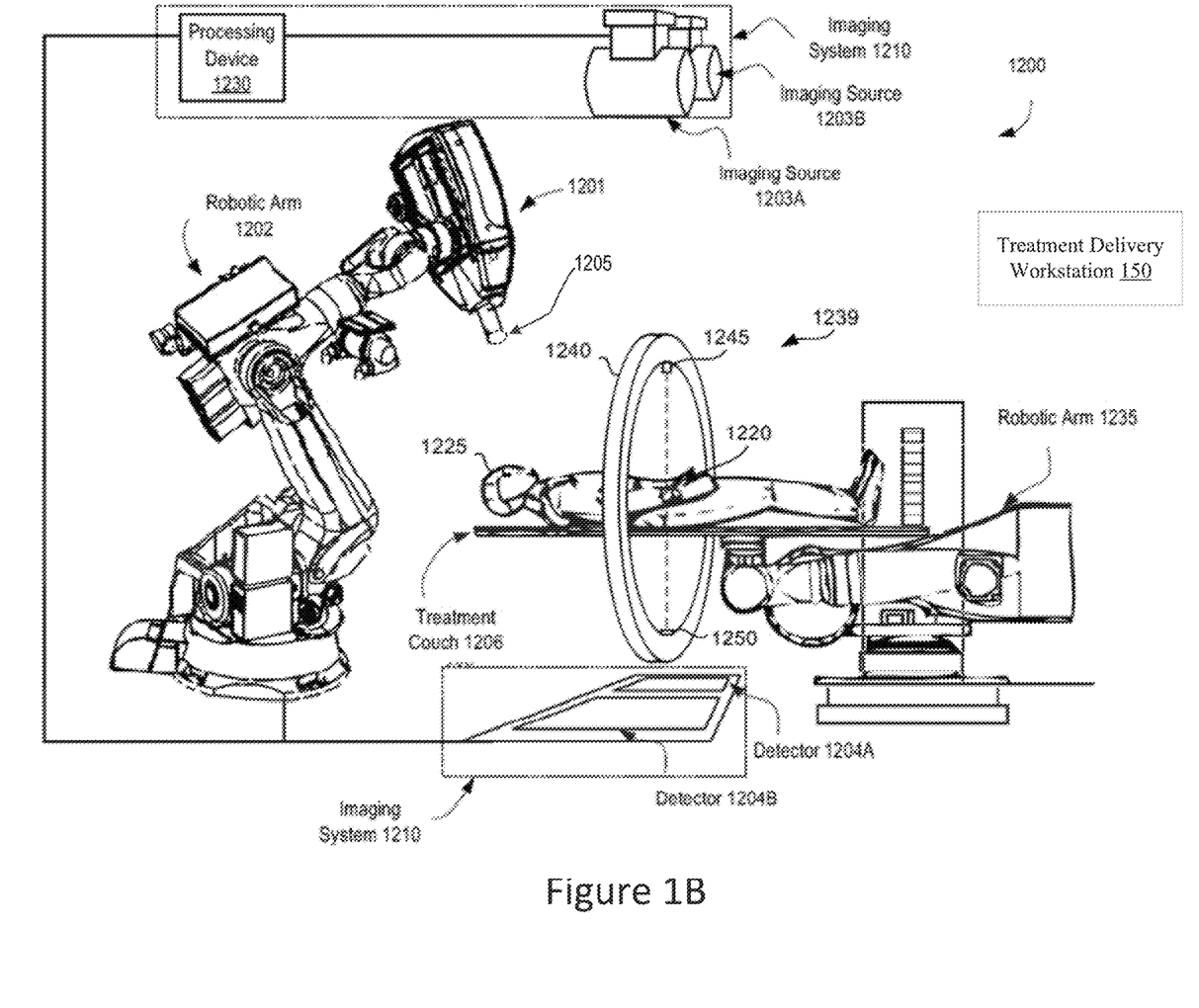
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 (e.g., an eMLC) coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3-D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2-D) or three-dimensional (3-D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI).

In other embodiments, imaging system 1210 may include more or less than two x-ray sources and more or less than two detectors, and any of the detectors may be movable rather than fixed. In yet other embodiments, the positions of the x-ray sources and the detectors may be interchanged.

Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3-D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240.

The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
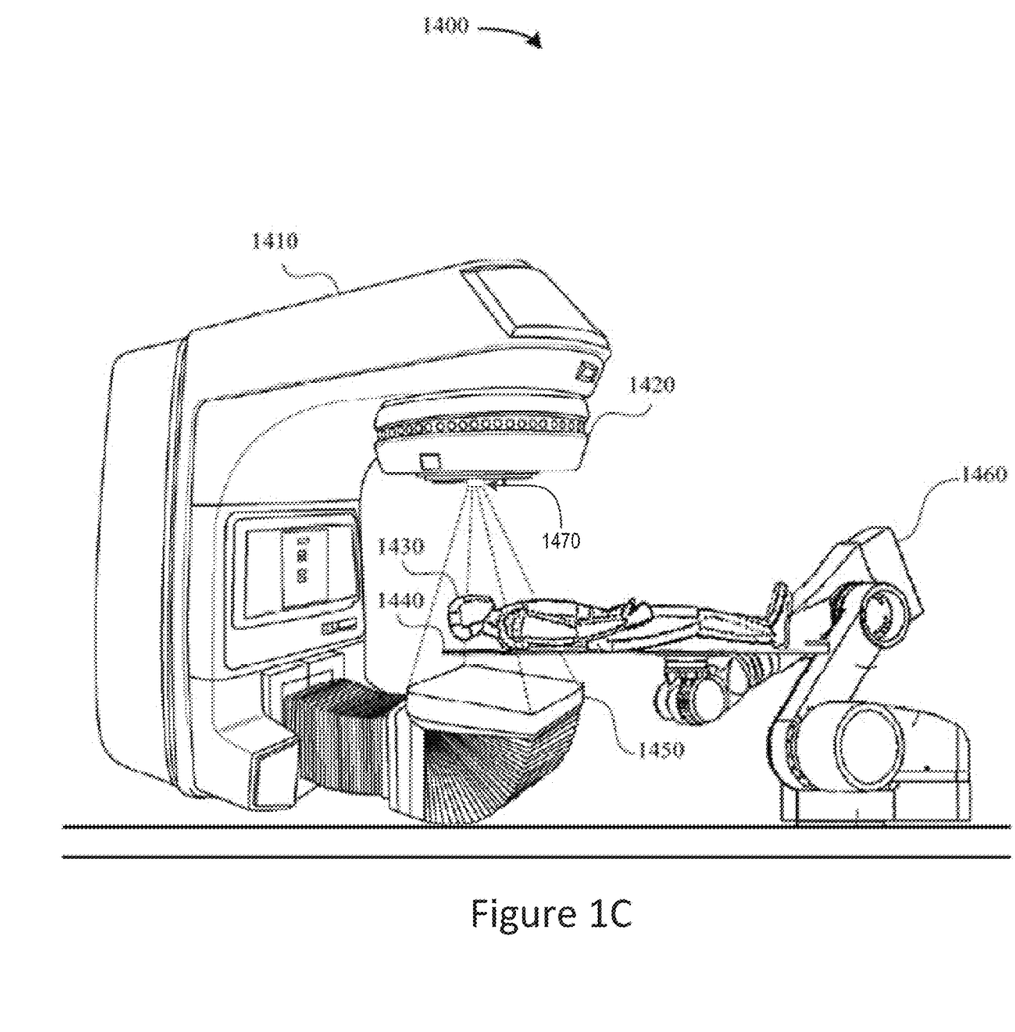
FIG. 1C illustrates a C-arm gantry-based radiation treatment system, in accordance with embodiments described herein.

FIG. 1C Illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a gantry 1410, a LINAC 1420, an MLC 1470 (e.g., an eMLC) coupled with the distal end of the LINAC 1420 to shape the beam, and a portal imaging detector 1450. The gantry 1410 may be rotated to an angle corresponding to a selected projection and used to acquire an x-ray image of a VOI of a patient 1430 on a treatment couch 1440.

In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter.

Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

With respect to the systems described above and herein, in one embodiment, a radiation treatment delivery system (e.g., of any suitable type) may include a memory to store information and a processing device, operatively coupled to the memory. In a variety of embodiments, the processing device and memory may be configured/programmed to perform any number of operations. For example, in one embodiment, the processing device may identify a treatment planning image of a target subject, the treatment planning image comprising the information associated with an arrangement of structures within the target subject. The processing device may further generate, based on the information, a set of reference data associated with the target subject, the reference data indicating a plurality of positions of the target subject.

The processing device may further generate a first target-subject-specific model based on the reference data and apply the first target-subject-specific model to the treatment planning image to generate a transformed treatment planning image corresponding to a first position of the plurality of positions. The processing device may further compare the transformed treatment planning image to a reference image. The processing device may further, based on the comparing, modify one or more hyper-parameters of the first target-subject-specific model to generate a second target-subject-specific model corresponding to a second position of the plurality of positions. The processing device may further control a radiation treatment delivery device based on the second target-subject-specific model to deliver a radiation treatment to the target subject.

In one embodiment, the treatment planning image may be one of three-dimensional (3-D) or four-dimensional (4-D) anatomical images and the transformed treatment planning image and the reference image may be two-dimensional (2-D) images. In one embodiment, the processing device nay further construct the first target-subject-specific model from a 3-D, 4-D, or other derived image of the target subject. In another embodiment, the processing device may further construct the first target subject-specific model from at least one deformable registration between the target subject and another subject. In another embodiment, the processing device may further construct the first target-subject-specific model from at least one deformable registration between the target subject at a first time and the target subject at a second time. In yet another embodiment, the processing device may further construct the first target subject-specific model from at least one deformable registration between the target subject and a synthesized atlas subject.

In one embodiment, the subject-specific models described herein may include a central atlas of the target subject and a set of basis transformations and appearance changes, and the processing device may further linearly combine the central atlas, the set of basis transformations, and the appearance changes to generate an estimate of one or more conformations in which the target subject may be found. In one embodiment, the subject-specific models may be developed using dimensionality reduction on a set of at least one of: real or synthetic data.

In one embodiment, the information and one or more parameters of the target-subject-specific models may be used to construct a fully 4-D spatiotemporal correspondence mapping between an anatomy of the target subject at a reference time and the anatomy of the target subject at time of image acquisition. The information and one or more parameters of the target-subject-specific models may further be used to construct a fully 4-D spatiotemporal appearance model of the target subject at a time of image acquisition.

In one embodiment, the processing device may further receive an auxiliary anatomical or pseudo-anatomical signal simultaneously with receiving the information. The auxiliary signal may be correlated with the first target-subject-specific model and the information to increase a temporal resolution of the second target-subject-specific model. Further, the auxiliary signal may be obtained optically based on a set of triangulated light-emitting diode (LED) markers.

As described herein, the radiation treatment system may optionally include a gantry coupled to the radiation source, wherein the gantry is configured to rotate the radiation source about the target subject. In one embodiment, the gantry includes a C-arm gantry. In another embodiment, the gantry includes a ring gantry. The radiation treatment system may optionally include a robotic arm coupled to the radiation source, wherein the robotic arm is configured to position the radiation source at a plurality of positions along a circular or elliptical trajectory. In one embodiment, the robotic arm positions the radiation source at the plurality of positions about the target subject. The radiation beam (e.g., from the radiation source) may include a kilovolt (kV) treatment beam. The MLC may include a binary MLC. Any other suitable combinations of equipment and functionality are further contemplated herein.

Figure 2:
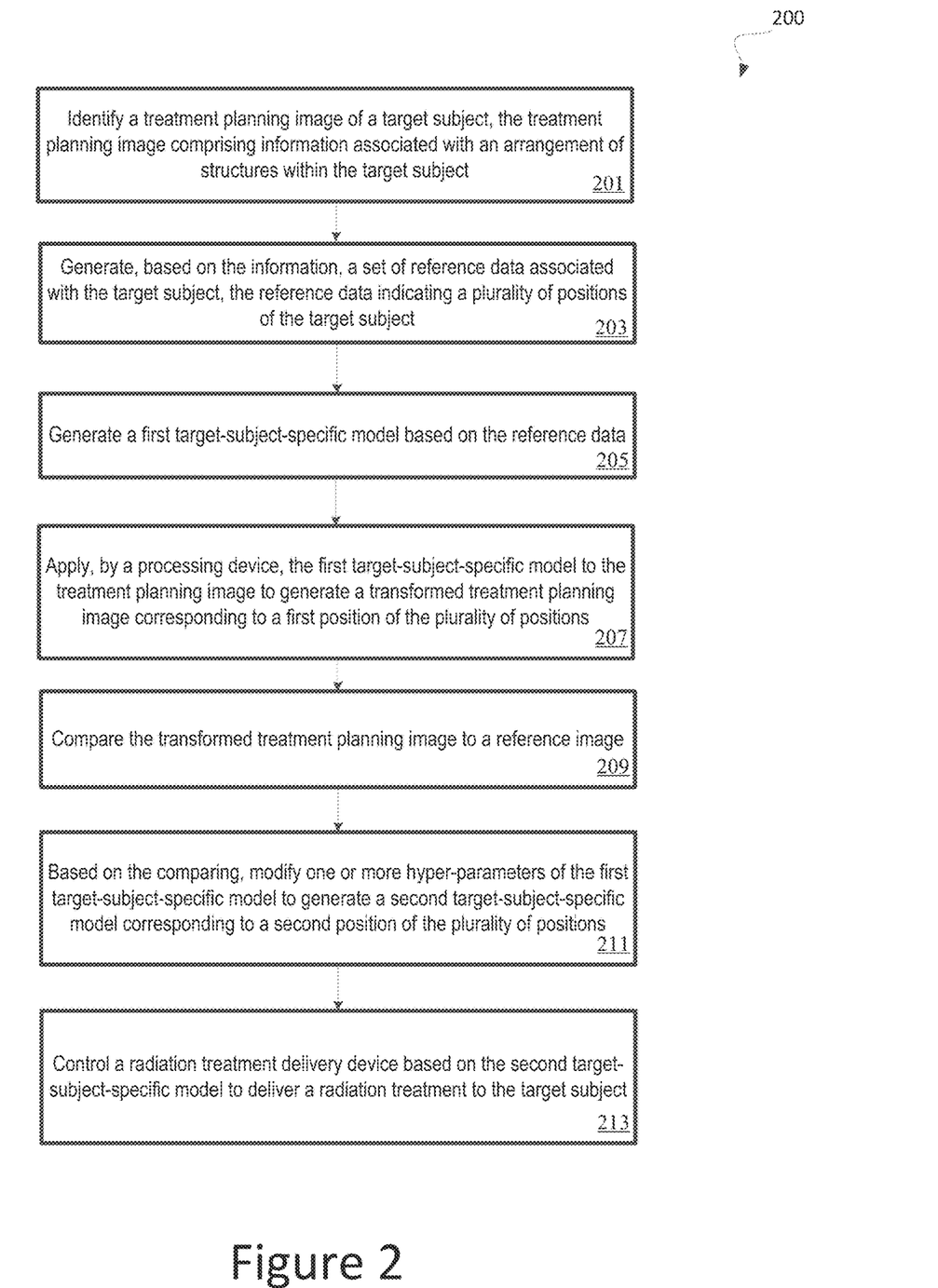
FIG. 2 depicts a first flow diagram of a method of generating a partial deformation map for reconstructing motion-affected treatment dose, in accordance with embodiments of the disclosure.

FIG. 2 depicts a first flow diagram of a method 200 of generating a partial deformation map for reconstructing motion-affected treatment dose, in accordance with embodiments of the disclosure. In general, the method 200 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 200 may be performed by processing logic of the radiation treatment system 800 of FIG. 1A.

As shown in FIG. 2, the method 200 may begin at block 201 with the processing logic identifying a treatment planning image of a target subject. In one embodiment, the treatment planning image may include information associated with an arrangement of structures within the target subject. In one embodiment, the treatment planning image is one of three-dimensional (3-D) or four-dimensional (4-D) anatomical images and wherein the transformed treatment planning image and the reference image are two-dimensional (2-D) images.

At block 203, processing logic may generate, based on the information, a set of reference data associated with the target subject, the reference data indicating a plurality of positions of the target subject. For example, in one embodiment, processing logic may gather the target images and register them together to generate a subject specific model, amongst other methods. This may be the data itself, and processing logic may also generate synthetic data, for example, using the PCA method. Processing logic may then perform PCA on the transformations. Bases produced by PCA may then be used to generate new transformations.

In one embodiment, the plurality of positions of the target subject represent any number of body shapes, contortions, translations, deformations, etc. that may be possible for any number of target subjects. The plurality of positions may represent a library of such, to be applied in future transformations as described. In one embodiment, the library of positions may include data from any number of target subjects and/or patients, and may be equally applied to any number of target subjects and/or patients. It is not required that only positions referring to a specific target subject be applied to that target subject. Positions referring to a first target subject may be applied to a second target subject, and vice a versa.

At block 205, processing logic may generate a first target-subject-specific model based on the reference data (which may include other target subjects' data, as described). One possible way in which the first target-subject-specific model may be generated is the PCA embodiment described above, in which the images from a RCCT are all registered together and PCA is performed on the resulting transformations. Other suitable methods are also contemplated.

At block 207, processing logic may apply the first target-subject-specific model to the treatment planning image to generate a transformed treatment planning image corresponding to a first position (e.g., a first likely position of the target subject) of the plurality of positions. In one embodiment, the system produces a transformation. The transformation is applied to each point in the target space. This produces the corresponding point in the planning space. The value of the planning image is then computed at that point and placed in the output buffer in target space.

Processing logic of block 209 may then compare the transformed treatment planning image to a reference image to determine an estimated accuracy of the transformed treatment planning image. In one embodiment, this may be determined by any suitable "image match" function that attempts to measure how well the transformed image matches the reference image. The basic one would be sum of squared differences, where processing logic may subtract the two images at each pixel, square the differences and add them all up. In other embodiments, processing logic may use machine learning to learn an image match function.

Based on the comparing, processing logic at block 211 may modify one or more hyper-parameters (e.g., parameters associated with one or more positions of one or more target subjects) of the first target-subject-specific model to generate a second target-subject-specific model corresponding to a second position of the plurality of positions. In one embodiment, the second position may be a more accurate representation of a current target subject position than the first position. Processing logic of block 213 may then control a radiation treatment delivery device based on the second target-subject-specific model to deliver a radiation treatment to the target subject. In one embodiment, the subject-specific models may be developed using dimensionality reduction on a set of at least one of: real or synthetic data.

In one embodiment, the information and one or more (hyper) parameters of the target-subject-specific models may be used to construct a fully 4-D spatiotemporal correspondence mapping between an anatomy of the target subject at a reference time and the anatomy of the target subject at time of image acquisition. Furthermore, the information and one or more parameters of the target-subject-specific models may be optionally used to construct a fully 4-D spatiotemporal appearance model of the target subject at a time of image acquisition.

Figure 3:
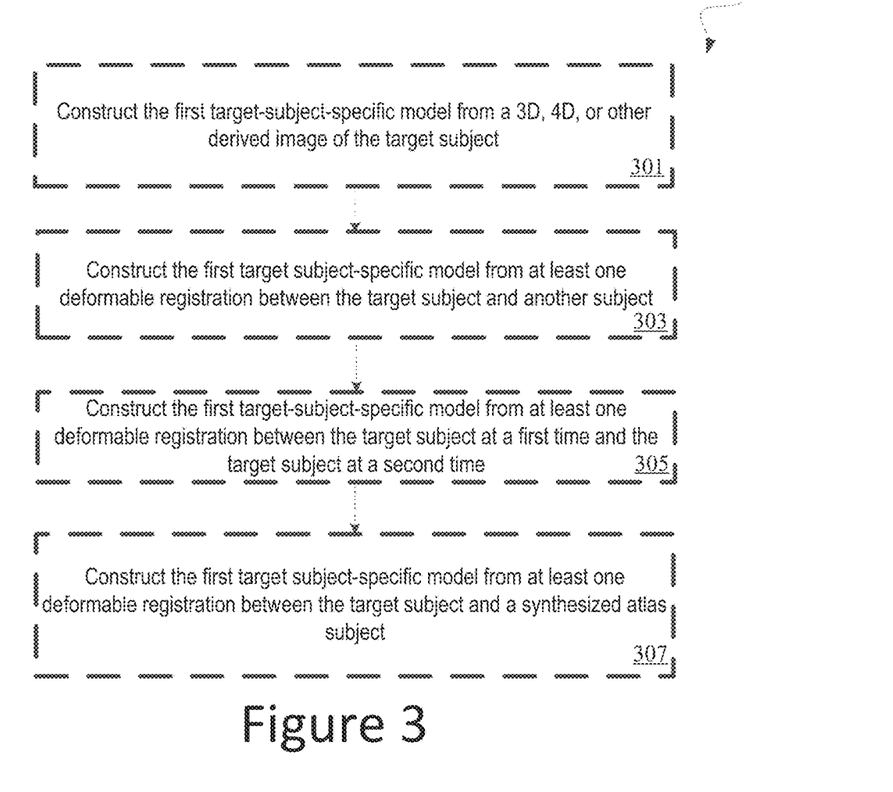
FIG. 3 depicts a second flow diagram of a method of generating a partial deformation map for reconstructing motion-affected treatment dose, in accordance with embodiments of the disclosure.

FIG. 3 depicts a second flow diagram 300 of a method of generating a partial deformation map for reconstructing motion-affected treatment dose, in accordance with embodiments of the disclosure. In general, the method 300 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 300 may be performed by processing logic of the radiation treatment system 800 of FIG. 1A. In one embodiment, method 300 optionally supplements method 200 of FIG. 2 and/or method 400 of FIG. 4.

As shown in FIG. 3, the method 300 may begin at block 301 with the processing logic constructing the first target-subject-specific model (e.g., from block 205 of FIG. 200) from a 3-D, 4-D, or other derived image of the target subject. Alternatively, or additionally, at block 303, processing logic may construct the first target subject-specific model from at least one deformable registration between the target subject and another subject. Alternatively, or additionally, at block 305, processing logic may construct the first target-subject-specific model from at least one deformable registration between the target subject at a first time and the target subject at a second time. Alternatively, or additionally, at block 307, processing logic may construct the first target subject-specific model from at least one deformable registration between the target subject and a synthesized atlas subject.

Figure 4:
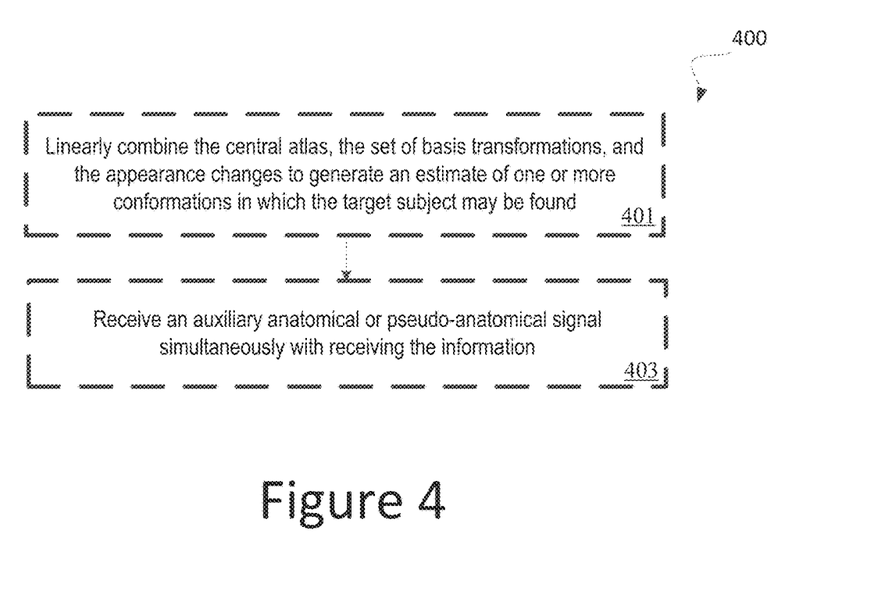
FIG. 4 depicts a third flow diagram of a method of generating a partial deformation map for reconstructing motion-affected treatment dose, in accordance with embodiments of the disclosure.

FIG. 4 depicts a third flow diagram of a method 400 of generating a partial deformation map for reconstructing motion-affected treatment dose, in accordance with embodiments of the disclosure. In general, the method 400 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 400 may be performed by processing logic of the radiation treatment system 800 of FIG. 1A. In one embodiment, method 400 optionally supplements method 200 of FIG. 2 and/or method 300 of FIG. 3.

In one embodiment, the subject-specific models (e.g., of blocks 205, 207, 211, and 213 of FIG. 2) comprise a central atlas of the target subject and a set of basis transformations and appearance changes. Processing logic at block 401 or Figure may then linearly combine the central atlas, the set of basis transformations, and the appearance changes to generate an estimate of one or more conformations in which the target subject may be found. At block 403, processing logic may optionally receive an auxiliary anatomical or pseudo-anatomical signal simultaneously with receiving the information. The auxiliary anatomical or pseudo-anatomical signal may have any number of suitable characteristics. For example, in one embodiment, the auxiliary signal may be correlated with the first target-subject-specific model and the information to increase a temporal resolution of the second target-subject-specific model. In another embodiment, the auxiliary signal is obtained optically based on a set of triangulated light-emitting diode (LED) markers.

Referring now to the methods 200, 300, and 400 described herein, a variety of optional embodiments are described. For example, a refinement of prior 4-D CT images and 4-D deformation maps with limited view data is described. This concept focuses on improving an ability to calculate a time dependent deformation map for patient anatomy influenced by respiratory or other periodic motion. In one embodiment, in order to simplify the difficulty associated with reconstructing a 3-D deformation map from one or a limited number of 2-D projection views, this disclosure provides for using a previously acquired 4-D CT and corresponding set of 3-D deformation maps. The idea is to determine the breathing phase most closely matching a view or sequence of views (e.g., using an external amplitude measurement or directly by comparing the view to digitally reconstructed radiographies (DRRs)); then making small adjustments to the deformation map associated with that breathing phase to better match the DRR of the deformed 3-D image to the observed 2-D view(s). These small adjustments to the deformation map can be further constrained to favor the directions of motion already present in present between adjacent phases of the 4-D CT and associated 4-D deformation maps.

One benefit of this approach is to enable estimation of patient deformation from one or a small handful of views. Another benefit is that it could enable deformable motion estimation on slow rotating imaging systems, such as TomoTherapy or cone-beam CT systems.

Another optional enhancement includes using partial deformation maps for reconstructing motion-affected treatment dose. This concept focuses on using the limited image data that may be available when acquired simultaneously during treatment to improve motion affected dose calculation. One observation is that most of the treatment dose delivered at any point in time is often limited to a small region of the patient. For example, on TomoTherapy, dose is delivered using a fan beam that only covers a fraction of the target at a time and is swept across the target over the course of the treatment delivery. If the patient is moving during treatment, the delivered dose is most affected by the movement occurring under the treatment beam at the moment the treatment beam is delivering its dose. So, for any time within the treatment delivery, one only needs to know the patient movement (e.g., deformation map) in the region under the treatment beam at that moment.

An exemplary embodiment of imaging the patient simultaneously with treatment delivery, and only having a limited field of view around the part of the patient simultaneously under the treatment beam is contemplated. It is possible to reconstruct a deformation map for the patient as they appear at each point in time, which only contains deformation data (or only contains accurate data) in the region around the target. For purposes of motion affected dose reconstruction, this may be sufficient to calculate the dose accurately, even though a complete deformation map of the patient at all times is not available.

In addition to only calculating the deformation for a limited field of view around the active treatment location, it may only be necessary to calculate the deformation in the two dimensions orthogonal to the treatment beam. In some embodiments, deformation in the direction parallel to the treatment beam may be less important, since dose gradients are small in this direction and will have less impact on the overall accuracy of the calculated dose. Advantageously, calculating the deformation in a limited number of dimensions could potentially have applications in other applications as well—e.g., motion tracking, real-time delivery adaptation, 4-D image reconstruction, etc.

Another optional enhancement includes using a 5-D model for 4-D CT and 4-D deformation directly from X-ray views. This concept focuses on improving an ability to calculate a time-dependent deformation map for patient anatomy influenced by respiratory or other periodic motion.

In some embodiments, a method for reconstructing time-dependent CT images (e.g., "4-D CTs") includes deriving a single phase 3-D CT plus a deformation function associated with each voxel dependent on an externally monitored breathing amplitude and breathing rate. This may be referred to as SDCT, referring to the 3 spatial dimensions+breathing amplitude+breathing rate. This method relies on already having 2-D image slices already reconstructed by a fast CT scanner (e.g., acquiring slices in a 'cine' acquisition mode).

In one embodiment, this novel concept does not rely on reconstructed 2-D image slices, and instead works directly on the 1-D or 2-D projection views acquired by the imaging system before reconstruction is performed. The concept is to simultaneously perform single phase CT image reconstruction and derive a time dependent deformation map, using the assumption that this deformation can be modeled as a linear function of amplitude and rate for each voxel to reduce the degrees of freedom and make the problem more tractable. One could contemplate this implemented as an iterative reconstruction, designed to update both the single phase CT and the deformation map functions each iteration until it converges. In one embodiment, the iterative update formula could use a gradient on the deformation map calculated by back projecting the deformations calculated in 2-D on each acquired 2-D view. In one embodiment the 3-D CT, reconstructed by ignoring motion, may be used as a starting point for the iterative optimization. One benefit of this approach is that it could work on slow rotating imaging systems, such as TomoTherapy or cone-beam CT systems.

Figure 5:
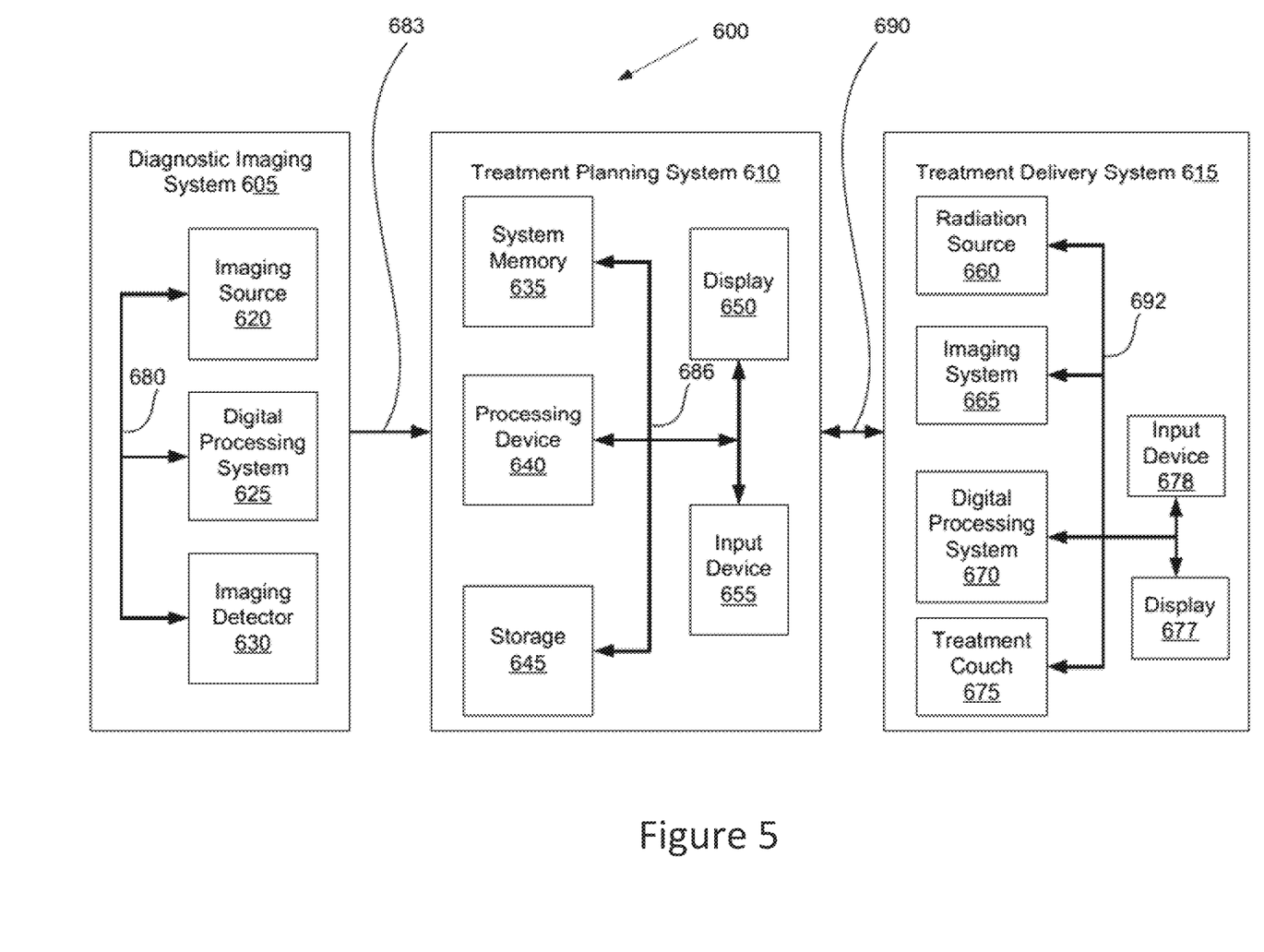
FIG. 5 illustrates examples of different systems that may be used to generate a partial deformation map for reconstructing motion-affected treatment dose, in accordance with embodiments described herein.

FIG. 5 illustrates examples of different systems 600 within which a set of instructions, for causing the systems to perform any one or more of the methodologies discussed herein, may be executed. In alternative implementations, the machine may be connected (e.g., networked) to other machines in a LAN, an intranet, an extranet, and/or the Internet. Each of the systems may operate in the capacity of a server or a client machine in client-server network environment, as a peer machine in a peer-to-peer (or distributed)

network environment, or as a server or a client machine in a cloud computing infrastructure or environment.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

As described below and illustrated in FIG. 5, a system 600 may include a diagnostic imaging system 605, a treatment planning system 610, and a treatment delivery system 615. Diagnostic imaging system 605 may be any system capable of producing medical diagnostic images of a patient that may be used for subsequent medical diagnosis, treatment planning, treatment simulation and/or treatment delivery. For example, diagnostic imaging system 605 may be a computed tomography (CT) system, a magnetic resonance imaging (MRI) system, a positron emission tomography (PET) system, a combination of such systems, or the like. For ease of discussion, diagnostic imaging system 605 may be discussed below at times in relation to an x-ray imaging modality. In other embodiments, other imaging modalities such as those discussed above may also be used.

In one embodiment, diagnostic imaging system 605 includes an imaging source 620 to generate an imaging beam (e.g., x-rays) and an imaging detector 630 to detect and receive the beam generated by imaging source 620, or a secondary beam or emission stimulated by the beam from the imaging source (e.g., in an MRI or PET scan).

In one embodiment, imaging source 620 and imaging detector 630 may be coupled to a digital processing system 625 to control the imaging operation and process image data. In one embodiment, diagnostic imaging system 605 may receive imaging commands from treatment delivery system 615 and/or treatment planning system 610.

Diagnostic imaging system 605 includes a bus or other means 680 for transferring data and commands among digital processing system 625, imaging source 620 and imaging detector 630. Digital processing system 625 may include one or more general-purpose processors (e.g., a microprocessor), special purpose processor such as a digital signal processor (DSP) or other type of processing device such as a controller or field programmable gate array (FPGA). Digital processing system 625 may also include other components (not shown) such as memory, storage devices, network adapters and the like. Digital processing system 625 may be configured to generate digital diagnostic images in a standard format, such as the Digital Imaging and Communications in Medicine (DICOM) format, for example.

In other embodiments, digital processing system 625 may generate other standard or non-standard digital image formats. Digital processing system 625 may transmit diagnostic image files (e.g., the aforementioned DICOM formatted files) to treatment delivery system 615 over a data link 683, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

In one embodiment, treatment delivery system 615 includes a therapeutic and/or surgical radiation source 660 to administer a prescribed radiation dose to a target volume in conformance with a treatment plan. Treatment delivery system 615 may also include imaging system 665 to perform computed tomography (CT) such as cone beam CT, and images generated by imaging system 665 may be two-dimensional (2-D) or three-dimensional (3-D).

Treatment delivery system 615 may also include a digital processing system 670 to control radiation source 660, receive and process data from diagnostic imaging system 605 and/or treatment planning system 610, and control a patient support device such as a treatment couch 675. Digital processing system 670 may be connected to or a part of a camera feedback system. Digital processing system 670 may be configured to perform any of the operations described herein. Digital processing system 670 may include a processing device that represents one or more general-purpose processors (e.g., a microprocessor), special purpose processor such as a digital signal processor (DSP) or other type of device such as a controller or field programmable gate array (FPGA). The processing device of digital processing system 670 may be configured to execute instructions to perform the operations described herein.

In one embodiment, digital processing system 670 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 670 may also include a storage device, representing one or more storage devices (e.g., a magnetic disk drive or optical disk drive) for storing information and instructions. The storage device may be used for storing instructions for performing the treatment delivery steps discussed herein. Digital processing system 670 may be coupled to radiation source 660 and treatment couch 675 by a bus 692 or other type of control and communication interface.

In one embodiment, the treatment delivery system 615 includes an input device 678 and a display 677 connected with digital processing system 670 via bus 692.

The display 677 can show trend data that identifies a rate of target movement (e.g., a rate of movement of a target volume that is under treatment). The display can also show a current radiation exposure of a patient and a projected radiation exposure for the patient. The input device 678 can enable a clinician to adjust parameters of a treatment delivery plan during treatment.

Treatment planning system 610 includes a processing device 640 to generate and modify treatment plans and/or simulation plans. Processing device 640 may represent one or more general-purpose processors (e.g., a microprocessor), special purpose processor such as a digital signal processor (DSP) or other type of device such as a controller or field programmable gate array (FPGA). Processing device 640 may be configured to execute instructions for performing simulation generating operations and/or treatment planning operations discussed herein.

Treatment planning system 610 may also include system memory 635 that may include a random access memory (RAM), or other dynamic storage devices, coupled to processing device 640 by bus 686, for storing information and instructions to be executed by processing device 640. System memory 635 also may be used for storing temporary variables or other intermediate information during execution of instructions by processing device 640. System memory 635 may also include a read only memory (ROM) and/or other static storage device coupled to bus 686 for storing static information and instructions for processing device 640.

Treatment planning system 610 may also include storage device 645, representing one or more storage devices (e.g., a magnetic disk drive or optical disk drive) coupled to bus 686 for storing information and instructions. Storage device 645 may be used for storing instructions for performing the treatment planning steps discussed herein.

Processing device 640 may also be coupled to a display device 650, such as a cathode ray tube (CRT) or liquid crystal display (LCD), for displaying information (e.g., a 2-D or 3-D representation of the VOI) to the user. An input device 655, such as a keyboard, may be coupled to processing device 640 for communicating information and/or command selections to processing device 640. One or more other user input devices (e.g., a mouse, a trackball or cursor direction keys) may also be used to communicate directional information, to select commands for processing device 640 and to control cursor movements on display 650.

Treatment planning system 610 may share its database (e.g., data stored in storage 645) with a treatment delivery system, such as treatment delivery system 615, so that it may not be necessary to export from the treatment planning system prior to treatment delivery. Treatment planning system 610 may be linked to treatment delivery system 615 via a data link 690, which in one embodiment may be a direct link, a LAN link or a WAN link.

It should be noted that when data links 683, 686, and 690 are implemented as LAN or WAN connections, any of diagnostic imaging system 605, treatment planning system 610 and/or treatment delivery system 615 may be in decentralized locations such that the systems may be physically remote from each other. Alternatively, any of diagnostic imaging system 605, treatment planning system 610, and/or treatment delivery system 615 may be integrated with each other in one or more systems.

It will be apparent from the foregoing description that aspects of the present disclosure may be embodied, at least in part, in software. That is, the techniques may be carried out in a computer system or other data processing system in response to a processing device 625, 640, or 670 (see FIG. 5), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 670.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
   identifying a treatment planning image of a target subject, the treatment planning image comprising information associated with an arrangement of structures within the target subject;
   generating, based on the information, a set of reference data associated with the target subject, the reference data indicating a plurality of positions of the target subject;
   generating a first target-subject-specific model based on the reference data;
   applying, by a processing device, the first target-subject-specific model to the treatment planning image to generate a transformed treatment planning image corresponding to a first position of the plurality of positions;
comparing the transformed treatment planning image to a reference image;
based on the comparing, modifying one or more hyperparameters of the first target-subject-specific model to generate a second target-subject-specific model corresponding to a second position of the plurality of positions; and
controlling a radiation treatment delivery device based on the second target-subject-specific model to deliver a radiation treatment to the target subject.

2. The method of claim 1, wherein the treatment planning image is one of three-dimensional (3-D) or four-dimensional (4-D) anatomical images and wherein the transformed treatment planning image and the reference image are two-dimensional (2-D) images.

3. The method of claim 1, further comprising constructing the first target-subject-specific model from a 3-D, 4-D, or other derived image of the target subject.

4. The method of claim 1, further comprising constructing the first target subject-specific model from at least one deformable registration between the target subject and another subject.

5. The method of claim 1, further comprising constructing the first target-subject-specific model from at least one deformable registration between the target subject at a first time and the target subject at a second time.

6. The method of claim 1, further comprising constructing the first target subject-specific model from at least one deformable registration between the target subject and a synthesized atlas subject.

7. The method of claim 1, wherein the subject-specific models comprise a central atlas of the target subject and a set of basis transformations and appearance changes, and wherein the method further comprises linearly combining the central atlas, the set of basis transformations, and the appearance changes to generate an estimate of one or more conformations in which the target subject may be found.

8. The method of claim 1, wherein the subject-specific models are developed using dimensionality reduction on a set of at least one of: real or synthetic data.

9. The method of claim 1, wherein the information and one or more parameters of the target-subject-specific models are used to construct a fully 4-D spatiotemporal correspondence mapping between an anatomy of the target subject at a reference time and the anatomy of the target subject at time of image acquisition.

10. The method of claim 1, wherein the information and one or more parameters of the target-subject-specific models are used to construct a fully 4-D spatiotemporal appearance model of the target subject at a time of image acquisition.

11. The method of claim 1, further comprising receiving an auxiliary anatomical or pseudo-anatomical signal simultaneously with receiving the information.

12. The method of claim 11, wherein the auxiliary signal is correlated with the first target-subject-specific model and the information to increase a temporal resolution of the second target-subject-specific model.

13. The method of claim 11, wherein the auxiliary signal is obtained optically based on a set of triangulated light-emitting diode (LED) markers.

14. A radiation treatment delivery system comprising:
a memory to store information; and
a processing device, operatively coupled to the memory, the processing device to:
identify a treatment planning image of a target subject, the treatment planning image comprising the information associated with an arrangement of structures within the target subject;
generate, based on the information, a set of reference data associated with the target subject, the reference data indicating a plurality of positions of the target subject;
generate a first target-subject-specific model based on the reference data;
apply the first target-subject-specific model to the treatment planning image to generate a transformed treatment planning image corresponding to a first position of the plurality of positions;
compare the transformed treatment planning image to a reference image;
based on the comparing, modify one or more hyperparameters of the first target-subject-specific model to generate a second target-subject-specific model corresponding to a second position of the plurality of positions; and
control a radiation treatment delivery device based on the second target-subject-specific model to deliver a radiation treatment to the target subject.

15. The radiation treatment delivery system of claim 14, wherein the treatment planning image is one of three-dimensional (3-D) or four-dimensional (4-D) anatomical images and wherein the transformed treatment planning image and the reference image are two-dimensional (2-D) images.

16. The radiation treatment delivery system of claim 14, the processing device further to construct the first target-subject-specific model from a 3-D, 4-D, or other derived image of the target subject.

17. The radiation treatment delivery system of claim 14, the processing device further to construct the first target subject-specific model from at least one deformable registration between the target subject and another subject.

18. The radiation treatment delivery system of claim 14, the processing device further to construct the first target-subject-specific model from at least one deformable registration between the target subject at a first time and the target subject at a second time.

19. The radiation treatment delivery system of claim 14, the processing device further to construct the first target subject-specific model from at least one deformable registration between the target subject and a synthesized atlas subject.

20. The radiation treatment delivery system of claim 14, wherein the subject-specific models comprise a central atlas of the target subject and a set of basis transformations and appearance changes, and wherein the processing device is further to linearly combine the central atlas, the set of basis transformations, and the appearance changes to generate an estimate of one or more conformations in which the target subject may be found.

21. The radiation treatment delivery system of claim 14, wherein the subject-specific models are developed using dimensionality reduction on a set of at least one of: real or synthetic data.

22. The radiation treatment delivery system of claim 14, wherein the information and one or more parameters of the target-subject-specific models are used to construct a fully 4-D spatiotemporal correspondence mapping between an anatomy of the target subject at a reference time and the anatomy of the target subject at time of image acquisition.

23. The radiation treatment delivery system of claim 14, wherein the information and one or more parameters of the target-subject-specific models are used to construct a fully 4-D spatiotemporal appearance model of the target subject at a time of image acquisition.

24. The radiation treatment delivery system of claim 14, the processing device further to receive an auxiliary anatomical or pseudo-anatomical signal simultaneously with receiving the information.

25. The radiation treatment delivery system of claim 24, wherein the auxiliary signal is correlated with the first target-subject-specific model and the information to increase a temporal resolution of the second target-subject-specific model.

26. The radiation treatment delivery system of claim 24, wherein the auxiliary signal is obtained optically based on a set of triangulated light-emitting diode (LED) markers.

27. The radiation delivery system of claim 14, further comprising:
a gantry coupled to the radiation source, wherein the gantry is configured to rotate the radiation source about the target subject.

28. The radiation delivery system of claim 27, wherein the gantry comprises a C-arm gantry.

29. The radiation delivery system of claim 27, wherein the gantry comprises a ring gantry.

30. The radiation delivery system of claim 14, further comprising:
a robotic arm coupled to the radiation source, wherein the robotic arm is configured to position the radiation source at a plurality of positions along a circular or elliptical trajectory.

31. The radiation delivery system of claim 30, wherein the robotic arm positions the radiation source at the plurality of positions about the target subject.

32. The radiation delivery system of claim 14, wherein the radiation beam comprises a kilovolt (kV) treatment beam.

33. The radiation delivery system of claim 14, wherein the MLC comprises a binary MLC.

34. A non-transitory, computer-readable storage medium comprising instructions, which when executed by a processing device, cause the processing device to:
identify a treatment planning image of a target subject, the treatment planning image comprising information associated with an arrangement of structures within the target subject;
generate, based on the information, a set of reference data associated with the target subject, the reference data indicating a plurality of positions of the target subject;
generate a first target-subject-specific model based on the reference data;
apply, by the processing device, the first target-subject-specific model to the treatment planning image to generate a transformed treatment planning image corresponding to a first position of the plurality of positions;
compare the transformed treatment planning image to a reference image;
based on the comparing, modify one or more hyperparameters of the first target-subject-specific model to generate a second target-subject-specific model corresponding to a second position of the plurality of positions; and
control a radiation treatment delivery device based on the second target-subject-specific model to deliver a radiation treatment to the target subject.

35. The non-transitory, computer-readable storage medium of claim 34, wherein the treatment planning image is one of three-dimensional (3-D) or four-dimensional (4-D) anatomical images and wherein the transformed treatment planning image and the reference image are two-dimensional (2-D) images.

36. The non-transitory, computer-readable storage medium of claim 34, the processing device further to construct the first target-subject-specific model from a 3-D, 4-D, or other derived image of the target subject.

37. The non-transitory, computer-readable storage medium of claim 34, the processing device further to construct the first target subject-specific model from at least one deformable registration between the target subject and another subject.

38. The non-transitory, computer-readable storage medium of claim 34, the processing device further to construct the first target-subject-specific model from at least one deformable registration between the target subject at a first time and the target subject at a second time.

39. The non-transitory, computer-readable storage medium of claim 34, the processing device further to construct the first target subject-specific model from at least one deformable registration between the target subject and a synthesized atlas subject.

40. The non-transitory, computer-readable storage medium of claim 34, wherein the subject-specific models comprise a central atlas of the target subject and a set of basis transformations and appearance changes, and wherein the processing device is further to linearly combine the central atlas, the set of basis transformations, and the appearance changes to generate an estimate of one or more conformations in which the target subject may be found.

41. The non-transitory, computer-readable storage medium of claim 34, wherein the subject-specific models are developed using dimensionality reduction on a set of at least one of: real or synthetic data.

42. The non-transitory, computer-readable storage medium of claim 34, wherein the information and one or more parameters of the target-subject-specific models are used to construct a fully 4-D spatiotemporal correspondence mapping between an anatomy of the target subject at a reference time and the anatomy of the target subject at time of image acquisition.

43. The non-transitory, computer-readable storage medium of claim 34, wherein the information and one or more parameters of the target-subject-specific models are used to construct a fully 4-D spatiotemporal appearance model of the target subject at a time of image acquisition.

44. The non-transitory, computer-readable storage medium of claim 34, the processing device further to receive an auxiliary anatomical or pseudo-anatomical signal simultaneously with receiving the information.

45. The non-transitory, computer-readable storage medium of claim 44, wherein the auxiliary signal is correlated with the first target-subject-specific model and the information to increase a temporal resolution of the second target-subject-specific model.

46. The non-transitory, computer-readable storage medium of claim 44, wherein the auxiliary signal is obtained optically based on a set of triangulated light-emitting diode (LED) markers.

* * * * *